United States Patent [19]

Huff et al.

[11] 3,990,945

[45] Nov. 9, 1976

[54] ENZYMATIC HYDROLYSIS OF CELLULOSE

[75] Inventors: George F. Huff, Pittsburgh, Pa.; Naoki Yata, Toda, Japan

[73] Assignee: Bio Research Center Company Limited, Tokyo, Japan

[22] Filed: Sept. 18, 1975

[21] Appl. No.: 614,490

Related U.S. Application Data

[63] Continuation-in-part of Ser. No. 572,428, April 28, 1975, abandoned.

[52] U.S. Cl. ................................................ 195/33
[51] Int. Cl.² ........................................ C12D 13/02
[58] Field of Search............... 195/66 R, 65, 62, 33, 195/7, 11; 210/11, 2, 3

[56] References Cited

UNITED STATES PATENTS

| | | | |
|---|---|---|---|
| 3,462,275 | 8/1969 | Bellamy | 210/11 X |
| 3,734,831 | 5/1973 | Hulme | 195/33 X |
| 3,764,475 | 10/1973 | Mandels et al. | 195/33 |
| 3,812,013 | 5/1974 | Bellamy et al. | 195/66 R |

OTHER PUBLICATIONS

Griffin et al., "Cellulase Production by Trichoderma Viride on Feedlot Waste", *Applied Microbiology,* vol. 27, No. 6, pp. 1061–1066 (1974).

Toyama et al., "Utilization of Cellulosic Wastes by Trichoderma Viride", *Proc. IVIFS: Ferment. Technol. Today,* pp. 743–757, (1972).

Mandels et al., "Enzymatic Hydrolysis of Waste Cellulose", *Biotechnology and Bioengineering,* vol. 16, pp. 1471–1493, (1974).

*Primary Examiner*—A. Louis Monacell
*Assistant Examiner*—Thomas G. Wiseman

[57] ABSTRACT

In the enzymatic hydrolysis of cellulose to obtain water-soluble sugars, the enzyme source is the aqueous culture mass obtained in an enzyme preparation step by cultivating in an aqueous nutrient medium in the presence of a cellulosic material a cellulolytic microorganism capable of elaborating a cellulolytic enzyme complex which can degrade native cellulose. No separation is made of any component of the culture mass. Such use of the culture mass as the enzyme source not only eliminates processing steps to separate the enzyme, but also results in increased hydrolysis rates and yields of the desired water-soluble sugars in the hydrolysis of cellulose.

3 Claims, 1 Drawing Figure

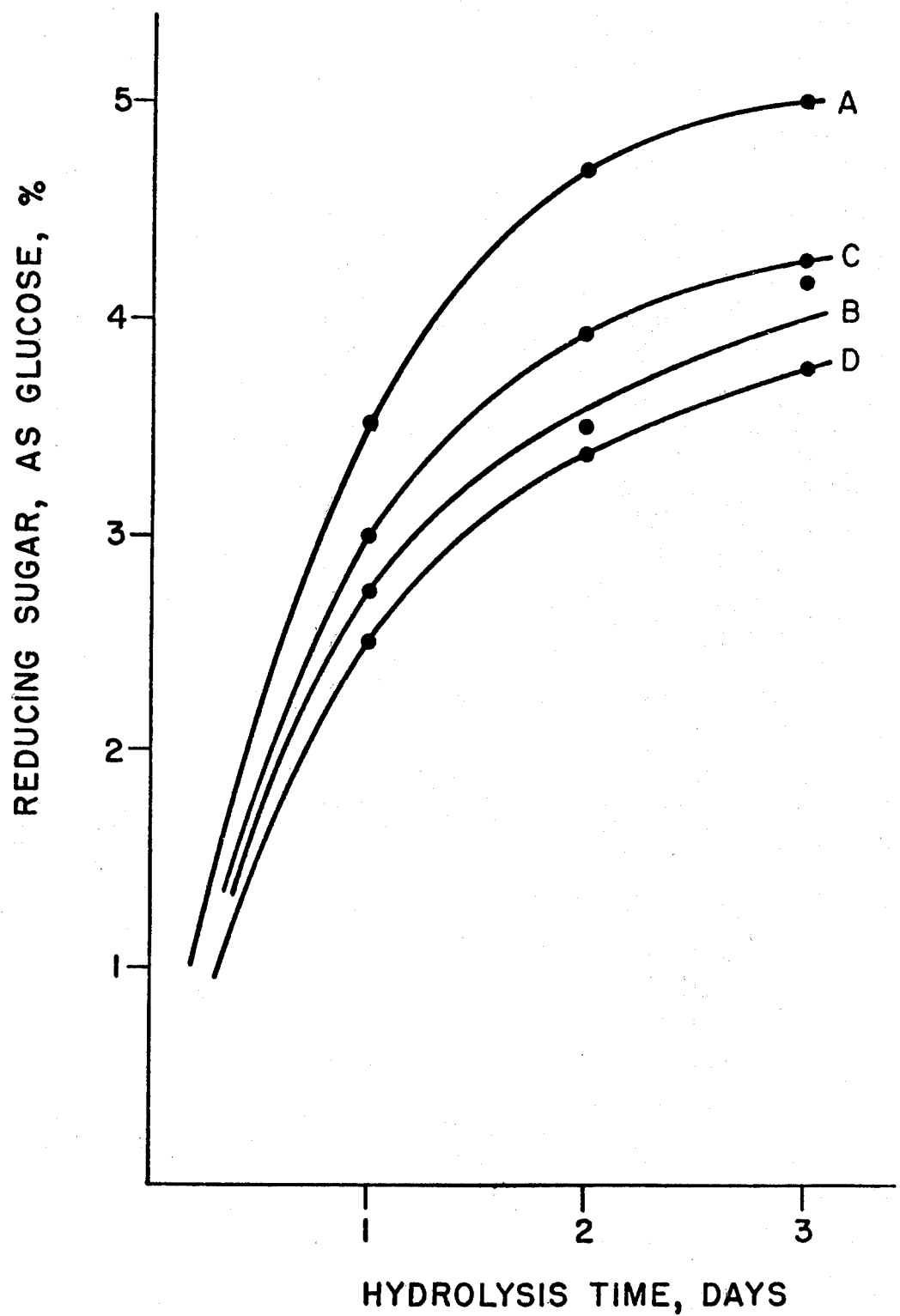

ENZYMATIC HYDROLYSIS OF CELLULOSE

This application is a continuation-in-part of copending application Ser. No. 572,428, filed Apr. 28, 1975, now abandon, and assigned to the same assignee as the present application.

BACKGROUND OF THE INVENTION

This invention relates to the enzymatic hydrolysis of cellulose to obtain water-soluble sugars.

There has been considerable interest in the development of a process which will take advantage of the natural abundance of cellulose and the mild reaction conditions utilized in enzymatically hydrolyzing or saccharifying cellulose to simple sugars such as glucose. For example, Ghose, U.S. Pat. No. 3,642,580, discloses a saccharification process wherein a concentrated cellulase enzyme solution is employed to hydrolyze finely divided dry cellulose to obtain a cellulose-cellulase-sugar slurry which is then subjected to ultrafiltration under pressure to separate the sugar syrup from the insoluble cellulose and soluble enzyme components, thereby allowing reuse of the enzyme. Mandels and Kostick, U.S. Pat. No. 3,764,475, disclose a similar process which eliminates the ultrafiltration step of Ghose by continuously adding dry cellulose during hydrolysis to immobilize the cellulase enzyme by adsorption on excess unhydrolyzed cellulose. More recently, in an article appearing in *Biotechnology and Bioengineering*, Vol. XVI, 1471–1493 (1974), November, 1974, Mandels, Hontz and Nystrom report on the use of pure and waste cellulose from various sources as a substrate for enzyme production and for enzymatic saccharification. It appears from these references that it has been considered necessary to separate the cellulase enzyme from the milieu in which it is produced prior to its use in hydrolyzing cellulose.

Toyama et al, *Proc. IV IFS: Ferment. Technology Today*, 743–757 (1972); report on the feasibility of producing sugars by the enzymatic saccharification of cellulosic wastes utilizing *Trichoderma viride* cellulase. On pages 753 and 754, there is disclosed the elaboration of enzyme in solid cultures on trays (Japanese koji type culture) and use of the entire solid culture so obtained as the enzyme source in a subsequent enzymatic saccharification of delignified cellulosic substrates. There is also disclosed the use of an aqueous extract of the enzyme from the same solid cultures in saccharifying the same delignified cellulosic substrates. Table 23 on page 753 shows the results obtained using the entire solid culturs. Table 24 on page 754 shows the results obtained using the aqueous enzyme extracts from the solid cultures. A comparison of Tables 23 and 24 with respect to the yields of sugar obtained shows that one solid culture, rice straw, gives lower yields than use of the aqueous enzyme extract from the same solid culture; with the other solid culture, rough printing paper, the reverse was true.

SUMMARY OF THE INVENTION

It has now been found that cellulose can be more effectively enzymatically hydrolyzed to water-soluble sugars when the enzyme employed is used in the hydrolysis reaction in the form of the aqueous culture mass obtained when an extracellular cellulolytic enzyme complex capable of degrading native cellulose is prepared in a separate enzyme preparation step by cultivating in an aqueous nutrient medium in the presence of a cellulosic material a cellulolytic microorganism capable of elaborating such enzyme complex. In other words, as the enzyme source, the crude aqueous enzyme preparation or an aliquot thereof is used directly in the saccharification reaction without separation of any of its components. If fact, except for the possible need to adjust the pH of the culture mass to that normally used in the enzymatic saccharification of cellulose, no other pretreatment of the enzyme preparation is necessary. Not only are processing steps such as filtration and concentration of enzyme rendered unnecessary, but the hydrolysis rate and yield of water-soluble sugars obtained are unexpectedly increased.

BRIEF DESCRIPTION OF THE DRAWINGS

The single FIGURE shows a graphic comparison of the rates of hydrolysis and yields of water-soluble reducing sugars obtained in the enzymatic hydrolysis of cellulose using the enzyme preparation of the invention and the enzyme culture filtrates heretofore employed.

DETAILED DESCRIPTION

The cellulolytic enzyme complex utilized in the enzymatic hydrolysis of cellulose in accordance with this invention is one capable of degrading native cellulose. As such, it contains the so-called $C_1$ and $C_x$ components referred to in the Mandels et al patent and article cited above. As is known in the art, these enzyme complexes are elaborated by such known and publicly available cellulolytic microorganisms as *Trichoderma viride*, *Trichoderma koningii*, *Fusarium solani*, *Fusarium javanicum*, and the like. Typical strains are *T.viride* QM6a, (ATCC 13,631), *T.koningii* (ATCC 18,649), *F.solani* (ATCC 16,372) and *F.javanicum* (ATCC 22,403). *T.viride* QM9123 (ATCC 24,449) and *T.viride* QM9414 (ATCC 26,921) are preferred. As used herein, the term "cellulolytic microorganism" means a microorganism which elaborates a cellulolytic enzyme complex capable of degrading native, crystalline cellulose.

The manner of preparing the aqueous culture mass containing the cellulolytic enzyme complex is itself conventional, the cellulolytic microorganism being cultivated in known manner in an aqueous nutrient medium in the presence of a cellulosic material in shake flasks or by submerged culture. Typical methods are shown in an article by Mandels and Weber, *Advances in Chemistry Series*, ACS 95, 391–414 (1969). After cultivation is completed, the aqueous culture mass or an aliquot thereof is employed directly in the cellulose saccharification step without further treatment except to adjust the pH if that is necessary. Thus, it is unnecessary and undesirable to filter off the mycelium or cellulosic material.

Other than the requirement that the aqueous culture mass is employed as the enzyme source, the enzymatic hydrolysis conditions employed are conventional. These conditions usually involve an aqueous medium having a pH in the range of about 4.8 to 5.2, with 5 being optimum, a temperature in the range of 25° to 50° C., preferably 45° to 50° C., a cellulolytic enzyme complex concentration of from 0.01 to 5 percent by weight of the reaction mixture and a cellulosic substrate concentration of from about 1 to 30 percent by weight.

Sources of cellulose for both preparation of the aqueous enzyme culture mass and the enzymatic hydrolysis can be either relatively pure or waste cellulosic materials, as shown in the Toyama et al and Mandels, Hontz and Nystrom articles cited. For example, Solka Floc purified sprucewood cellulose, Avicel microcrystalline cellulose, newsprint, newspaper, fiberboard, milk cartons, paper mill waste, cellulose fibers from the wet or dry shredding of municipal trash, and the like are successfully employed.

DESCRIPTION OF PREFERRED EMBODIMENTS

The following examples are illustrative of the invention.

Example 1

An aqueous enzyme culture mass was prepared as follows.

To each of two potato dextrose agar slants of *T.viride* QM9123, there was added 5 ml. of sterilized water. After shaking, the resulting suspensions were combined and added to 10 ml. of a CaCl trace metal solution having the following composition:

| | |
|---|---|
| $FeSO_4 \cdot 7H_2O$ | 250 mg. |
| $MnSO_4 \cdot H_2O$ | 80 mg. |
| $ZnSO_4 \cdot 7H_2O$ | 70 mg. |
| $CoCl_2 \cdot 6H_2O$ | 100 mg. |
| Deionized Water | 500 ml. |

One ml. of the above mixture was then added to 1.5 g. of wet crude fiber diluted to 29 ml. with deionized water.

The wet crude fiber had been recovered from the wet shredding or pulping of municipal trash and had a solids content of 30.1 percent by weight. On a dry basis, it had a weight content of 10.3 percent lignin and 68.1 percent cellulose. Prior to being diluted with the deionized water, the wet crude fiber had been mixed with 100 ml. water, blended and then centrifuged.

To the mixture of *T.viride*, trace element solution, wet crude fiber and deionized water, there was added 20 ml. of an aqueous nutrient medium prepared as follows. Seventy (70) g. of $(NH_4)_2$-$SO_4$, 100 g. of $KH_2PO_4$, 15 g. of urea, 15 g. of $CaCl_2 \cdot 2H_2O$, 15 g. of $MgSO_4 \cdot 7H_2O$ and 37.5 g. of peptone were thoroughly mixed in a mortar, and 5.05 g. of the resulting mixture were dissolved in 400 ml. of deionized water to obtain the aqueous nutrient medium. Prior to inoculation with the *T.viride*, the nutrient solution and wet crude fiber were sterilized by heating to 121° C. for 15 minutes. Incubation then took place on a rotary shaker at 24° C. for a period of 7 days. The pH of the resulting culture mass was 5.22; the pH was adjusted to 5.0 by the addition of hydrochloric acid prior to its use as the enzyme source in hydrolyzing cellulose.

The entire aqueous enzyme culture mass was then divided into four portions for the ensuing enzymatic hydrolysis of cellulose. One portion (A) was used directly in the hydrolysis without further treatment. A second portion (B) was filtered through glass wool to remove mycelium and other insolubles; the resulting culture filtrate was used in the hydrolysis. A third portion (C) was subjected to ultra high frequency sound waves in a Model W185 Sonifier Cell Disrupter (Heat Systems - Ultrasonics, Inc., Plainview, N. Y.) using a standard microtip (Bronson Sonic Power Co., Danbury, Conn.) and then used in the hydrolysis. The ultrasonic treatment took place four times in 15 second bursts at a meter reading of 55 to 75 watts. The purpose of this treatment was to attempt to release any enzyme bound to the cell walls of the *T.viride* mycelia. The fourth portion (D) was subjected to the same ultrasonic treatment as the third, but was then filtered through glass wool to remove insolubles. The resulting culture filtrate was employed in the hydrolysis.

For the hydrolysis, four separate portions of 300 mg. of a 200 mesh ball milled sprucewood cellulose pulp (Solka Floc BW 200, Brown Company, Berlin, N. H.) were added to 4 ml. of each of the above enzyme preparations to obtain four 7.5% (weight/volume) aqueous cellulose suspensions. The four mixtures were each buffered with 0.05 M acetate buffer, pH 5.0, and were incubated at 45° C. Samples were taken at 1, 2 and 3 days from each mixture, subjected to a boiling water bath for 5 minutes to inactivate the enzyme, and then analyzed for reducing sugars, measured as glucose, by a dinitrosalicylic acid method. [See G. L. Miller, *Anal. Chem.* 31, 426 (1959) ]. The results are shown in the following table.

| Enzyme Source | % Reducing Sugar, as Glucose | | |
|---|---|---|---|
| | Day 1 | Day 2 | Day 3 |
| A | 3.53 | 4.70 | 5.04 |
| B | 2.72 | 3.53 | 4.22 |
| C | 3.00 | 3.93 | 4.30 |
| D | 2.51 | 3.41 | 3.81 |

The single FIGURE of the drawing shows the data in the above table in graphic form.

From the data in the table and the drawing, it is apparent that the use of an entire aqueous culture mass as the cellulolytic enzyme source in accordance with this invention increases both the rate of cellulose hydrolysis and the yield of water-soluble sugars. For example, when the culture mass is simply filtered and the culture filtrate is employed as the enzyme source (Enzyme Source B, Curve B), as is conventional in this art, the rate of hydrolysis and yield of sugar are significantly lower than those obtained with the entire culture mass as the enzyme source (Enzyme Source A, Curve A). Although the use of ultrasonic waves decreases enzymatic activity (Enzyme Source C, Curve C), nevertheless an improvement in hydrolysis rate and sugar yield are shown over an otherwise identical enzyme source which has additionally been filtered and the culture filtrate then employed in the hydrolysis (Enzyme Source D, Curve D).

Example 2

Another aqueous enzyme culture mass was prepared substantially as in Example 1, except that cultivation continued for 18 days. The resulting culture mass had a pH of 5.58 which was adjusted to pH 5.0 by the addition of hydrochloric acid prior to its use in an enzymatic hydrolysis.

To two separate 4 ml. portions of the above aqueous culture mass there were separately added (1) 300 mg. of a 200 mesh ball milled sprucewood cellulose pulp (Solka Floc BW 200) to obtain a 7.5% (wt./vol.) pulp aqueous suspension, and (2) 300 mg. of dried crude fiber obtained from the same wet crude fiber of Example 1 to obtain a 7.5% (wt.vol.) crude fiber aqueous suspension. Prior to being dried, the wet crude fiber was blended with water, filtered through a coarse fritted glass filter, and the filter cake washed three times with 5 liters of distilled water for each washing. The two mixtures of culture mass and cellulosic material were incubated at 45° C. Samples were taken at 1, 2 and 3 days from each mixture, subjected to a boiling water bath for 5 minutes to inactivate the enzyme, and then analyzed for reducing sugars, measured as glucose, by the same dinitrosalicylic acid method mentioned in Example 1. The following results were obtained.

| Substrate | % Reducing Sugar, as Glucose | | |
|---|---|---|---|
| | Day 1 | Day 2 | Day 3 |
| Solka Floc | 3.74 | 4.93 | 5.39 |
| Dried Crude Fiber | 2.45 | 3.07 | 3.15 |

The above description shows that an entire aqueous culture mass, including the cellulolytic microorganism, the cellulosic carbon source and the aqueous nutrient medium can be successfully employed as the enzyme source in the enzymatic hydrolysis of cellulose. Increased hydrolysis rates and increased yields of water-soluble sugars are obtained.

What is claimed is:

1. In a process for the enzymatic hydrolysis of cellulose to obtain water-soluble sugars, wherein
   a. an extracellular cellulolytic enzyme complex capable of degrading native celulose is prepared in an enzyme prparation step by cultivating in an aqueous nutrient medium in the presence of a cellulosic material a cellulolytic microorganism capable of elaborating said enzyme complex to obtain an aqueous culture mass, and
   b. a cellulosic substrate is thereafter hydrolyzed in the presence of said enzyme complex under enzymatic hydrolysis conditions to obtain said sugars;
   the improvement which comprises:
   performing said enzyme preparation step and said hydrolysis step separately and utilizing in said hydrolysis step the aqueous culture mass of said enzyme preparation step or an aliquot thereof without separating any component thereof, thereby increasing the hydrolysis rate and the yield of water-soluble sugars in said hydrolysis step, and obtaining said sugars from said process.

2. The process of claim 1, wherein the cellulolytic microorganism is *Trichoderma viride*.

3. The process of claim 1, wherein the cellulosic material of the enzyme preparation step and the cellulosic substrate of the hydrolysis step are derived from waste cellulose.

* * * * *